(12) United States Patent
Wolfer

(10) Patent No.: US 11,369,505 B2
(45) Date of Patent: Jun. 28, 2022

(54) LUMBAR TRACTION DEVICE

(71) Applicant: Charles Wolfer, Arlington, TX (US)

(72) Inventor: Charles Wolfer, Arlington, TX (US)

( * ) Notice: Subject to any disclaimer, the term of this patent is extended or adjusted under 35 U.S.C. 154(b) by 494 days.

(21) Appl. No.: 16/599,199

(22) Filed: Oct. 11, 2019

(65) Prior Publication Data

US 2021/0106451 A1 Apr. 15, 2021

(51) Int. Cl.
*A47C 7/42* (2006.01)
*A47C 7/46* (2006.01)
*A61F 5/042* (2006.01)
*A47C 7/74* (2006.01)
*A61F 5/02* (2006.01)

(52) U.S. Cl.
CPC .............. *A61F 5/042* (2013.01); *A47C 7/46* (2013.01); *A47C 7/744* (2013.01); *A61F 5/024* (2013.01)

(58) Field of Classification Search
CPC .. A47C 7/42; A47C 7/425; A47C 7/46; A47C 7/462; A47C 7/744; A61H 1/02; A61F 5/024; A61F 5/042
USPC ...... 297/230.1–230.14, 284.4, 284.7; 601/32
See application file for complete search history.

(56) References Cited

U.S. PATENT DOCUMENTS

| | | | | |
|---|---|---|---|---|
| 1,356,365 A * | 10/1920 | Hosmer | ............... | A61H 1/0218 602/32 X |
| 2,756,809 A * | 7/1956 | Endresen | ............... | A47C 7/462 297/284.7 |
| 2,835,247 A * | 5/1958 | Stabholc | ............... | A61F 5/028 602/19 |
| 3,771,518 A * | 11/1973 | Greissing | ............ | A61H 1/0222 606/243 |
| 3,813,148 A * | 5/1974 | Kraus | ..................... | A47C 7/425 297/230.11 |
| 3,889,664 A * | 6/1975 | Heuser | ..................... | A61F 5/024 602/36 |
| 4,153,293 A * | 5/1979 | Sheldon | ................. | B60N 2/667 297/284.4 |
| 4,688,557 A * | 8/1987 | Bradstreet | ........... | A61H 1/0218 606/241 |
| 4,722,569 A * | 2/1988 | Morgenstern | .......... | A47C 7/462 297/284.7 |
| 4,981,148 A | 1/1991 | Fuller | | |
| 4,987,885 A * | 1/1991 | Shtabholz | ............... | A61F 5/024 606/241 |
| 5,088,476 A * | 2/1992 | Burton | ................. | A61H 1/0292 606/241 |

(Continued)

FOREIGN PATENT DOCUMENTS

WO  WO9522948  8/1995

*Primary Examiner* — Rodney B White

(57) ABSTRACT

A lumbar traction device for treating a lower back of a user includes a shell that is coupled to and extends from a rear edge of a panel. The shell and the panel are configured to position on a seat and in abutment a backrest of a chair, respectively. A coupling means that extends through a front of the shell is coupled to a plate positioned in the shell. The coupling means is configured to couple to a torso of the user to couple the user to the plate. An actuator, which is positioned in the shell and operationally coupled to the plate, is positioned to selectively raise the plate relative to the seat of the chair. The coupling means is configured to transmit an upward force from the actuator to the torso of the user to place a lumbar region of a spine of the user in traction.

16 Claims, 6 Drawing Sheets

(56) References Cited

U.S. PATENT DOCUMENTS

| | | | | |
|---|---|---|---|---|
| 5,171,317 A | * | 12/1992 | Corcoran | A61H 1/0292 606/241 X |
| 5,224,924 A | * | 7/1993 | Urso | A61H 1/0222 602/19 X |
| 5,344,211 A | * | 9/1994 | Adat | A47C 7/42 297/284.7 |
| 5,437,609 A | * | 8/1995 | Leonard | A61H 1/0292 606/241 |
| 5,462,518 A | * | 10/1995 | Hatley | A63B 21/4009 602/36 X |
| D398,804 S | | 9/1998 | Loud | |
| 5,848,984 A | * | 12/1998 | Bachar | A61F 5/01 602/32 |
| 6,315,750 B1 | * | 11/2001 | Gray | A61F 5/028 606/241 |
| 6,988,772 B2 | * | 1/2006 | Rutty | A47C 7/425 297/230.1 X |
| 7,097,628 B1 | * | 8/2006 | Baune | A61H 1/0218 602/32 X |
| 7,219,963 B2 | | 5/2007 | Fridd | |
| 7,237,848 B1 | * | 7/2007 | Story | B60N 2/665 297/284.3 |
| 7,357,777 B1 | * | 4/2008 | Meyers | A61H 1/0292 606/240 |
| 7,422,282 B2 | * | 9/2008 | Rutty | A47C 7/425 297/230.11 |
| 7,448,682 B2 | * | 11/2008 | Rutty | B60N 2/787 297/230.1 X |
| 7,469,963 B2 | * | 12/2008 | Rutty | B60N 2/787 297/230.14 |
| 7,540,564 B2 | | 6/2009 | Gokhale | |
| 7,601,132 B2 | * | 10/2009 | Nichols | A61H 1/0296 601/24 |
| 7,614,691 B1 | * | 11/2009 | Schmitz | A47C 7/021 297/230.13 X |
| 7,654,974 B2 | * | 2/2010 | Bass | A61H 1/0218 297/284.7 X |
| 7,686,393 B2 | * | 3/2010 | Rutty | A47C 7/425 297/230.11 |
| 7,758,119 B1 | * | 7/2010 | Baterdouk | A47C 7/425 297/230.12 |
| 7,909,399 B2 | * | 3/2011 | Rutty | A47C 7/425 297/230.11 |
| 8,459,737 B2 | * | 6/2013 | Brotsch | A47C 7/425 297/230.11 |
| 8,652,081 B2 | * | 2/2014 | Rawlings | A61F 5/024 602/32 X |
| 8,740,303 B2 | * | 6/2014 | Halliday | A47C 7/462 297/284.3 |
| 9,033,416 B1 | * | 5/2015 | Vanderhorst | A47C 7/46 297/230.11 |
| 9,149,125 B2 | | 10/2015 | Davis | A47C 7/46 |
| 9,198,515 B1 | * | 12/2015 | Vanderhorst | B60N 2/665 |
| 9,254,042 B2 | * | 2/2016 | Halliday | A47C 7/462 |
| 2004/0090098 A1 | * | 5/2004 | Rutty | A47C 7/425 297/230.1 |
| 2006/0055217 A1 | * | 3/2006 | Rutty | B60N 2/79 297/230.1 |
| 2006/0178603 A1 | * | 8/2006 | Popescu | A47C 7/465 601/84 |
| 2008/0129095 A1 | * | 6/2008 | Rutty | B60N 2/753 297/230.1 |
| 2008/0272635 A1 | * | 11/2008 | Rutty | B60N 2/787 297/230.1 |
| 2008/0303324 A1 | * | 12/2008 | Rutty | A47C 7/425 297/230.1 |
| 2011/0001341 A1 | * | 1/2011 | Jorgensen | A61G 5/1043 297/230.1 |
| 2011/0021961 A1 | * | 1/2011 | Rawlings | A61F 5/024 602/32 X |
| 2015/0238017 A1 | * | 8/2015 | Zouzal | B60N 2/665 297/230.1 X |

\* cited by examiner

LUMBAR TRACTION DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to traction devices and more particularly pertains to a new traction device for treating a lower back of a user.

(2) Description of Related Art Including Information Disclosed Under 37 CFR 1.97 and 1.98

The prior art relates to traction devices.

BRIEF SUMMARY OF THE INVENTION

An embodiment of the disclosure meets the needs presented above by generally comprising a shell that is coupled to and extends from a rear edge of a panel. The shell and the panel are configured to position on a seat and in abutment a backrest of a chair, respectively. A coupling means that extends through a front of the shell is coupled to a plate positioned in the shell. The coupling means is configured to couple to a torso of the user to couple the user to the plate. An actuator, which is positioned in the shell and operationally coupled to the plate, is positioned to selectively raise the plate relative to the seat of the chair. The coupling means is configured to transmit an upward force from the actuator to the torso of the user to place a lumbar region of a spine of the user in traction.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
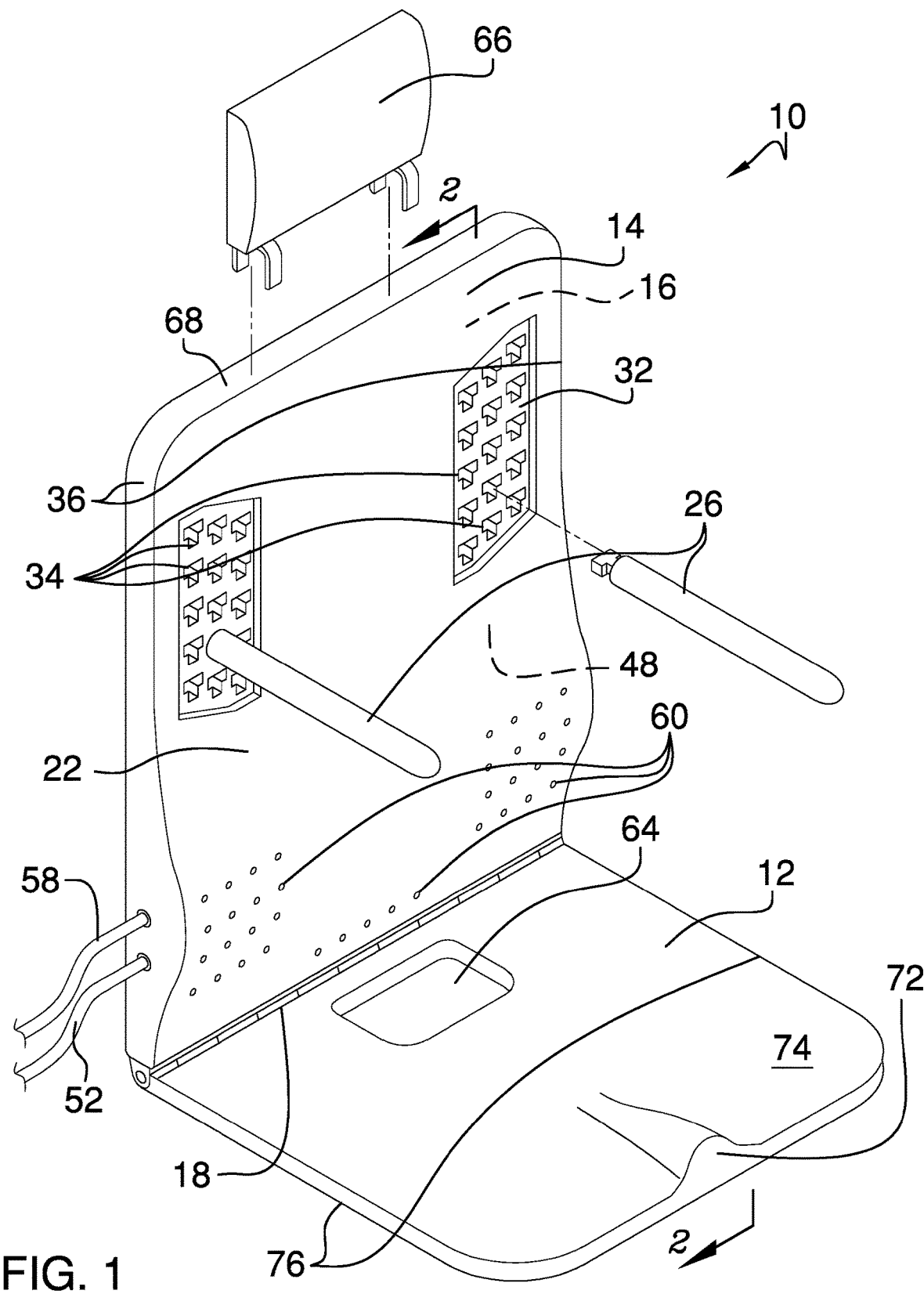
FIG. 1 is an isometric perspective view of a lumbar traction device according to an embodiment of the disclosure.

With reference now to the drawings, and in particular to FIGS. 1 through 6 thereof, a new traction device embodying the principles and concepts of an embodiment of the disclosure and generally designated by the reference numeral 10 will be described.

As best illustrated in FIGS. 1 through 6, the lumbar traction device 10 generally comprises a panel 12 that is configured to position on a seat of a chair. A shell 14, which defines an interior space 16, is coupled to and extends from a rear edge 18 of the panel 12. The shell 14 is configured to position in abutment to a backrest of the chair. The shell 14 is hingedly coupled to the panel 12 so that the shell 14 is configured to hinge relative to the panel 12 as the backrest is hinged relative to the seat. A lower section 20 of a front 22 of the shell 14 is convexly arcuate so that the lower section 20 is configured to support a lower back of the user.

A plate 24 is positioned in the interior space 16. A coupling means 26 is coupled to the plate 24 and extends through the front 22 of the shell 14. The coupling means 26 is configured to couple to a torso of a user who is seated upon the chair to couple the user to the plate 24. The coupling means 26 may comprise a pair of arms 28, as shown in FIG. 1, or other coupling means 26, such as straps, belts, and the like, which are configured to couple to at least one of an arm, a torso, a shoulder, and an abdomen of the user.

Each arm 28 is coupled to and extends from a forward face 30 of the plate 24 through an associated orifice 32 that is positioned in the shell 14. The arm 28 is configured to position in an associated armpit of the user who is seated upon the chair. The present invention anticipates the arms 28 being linear, as shown in FIG. 2, as well as curved, and of a variety of lengths and diameters.

Each of a set of first fasteners 34 is coupled to the plate 24 so that the first fastener 34 is accessible through an associated orifice 32 that is positioned proximate to an associated opposing side 36 of the shell 14. Each of a pair of second fasteners 38 is coupled to a terminus 40 of a respective arm 28. The second fastener 38 is complementary to the first fasteners 34 so that the second fastener 38 is positioned to selectively couple to a respective first fastener 34 to removably couple the respective arm 28 to the plate 24. The second fastener 38 being selectively couplable to the first fastener 34 positions the user to couple the respective arm 28 to the plate 24 so that the respective arm 28 is positioned to insert into the associated armpit of the user.

The second fastener 38 may comprise a bar 42 that is coupled to and extends from the terminus 40 of the respective arm 28. The bar 42 is T-shaped. The respective first fastener 34 may comprise a slot 44 that is positioned in the plate 24. The slot 44 is T-shaped so that the slot 44 is positioned to selectively insert the bar 42 to removably couple the respective arm 28 to the plate 24. The second fastener 38 and the respective first fastener 34 may together comprise other fastening means, such as, but not limited to threaded fasteners, hooking fasteners, and the like.

Figure 2:
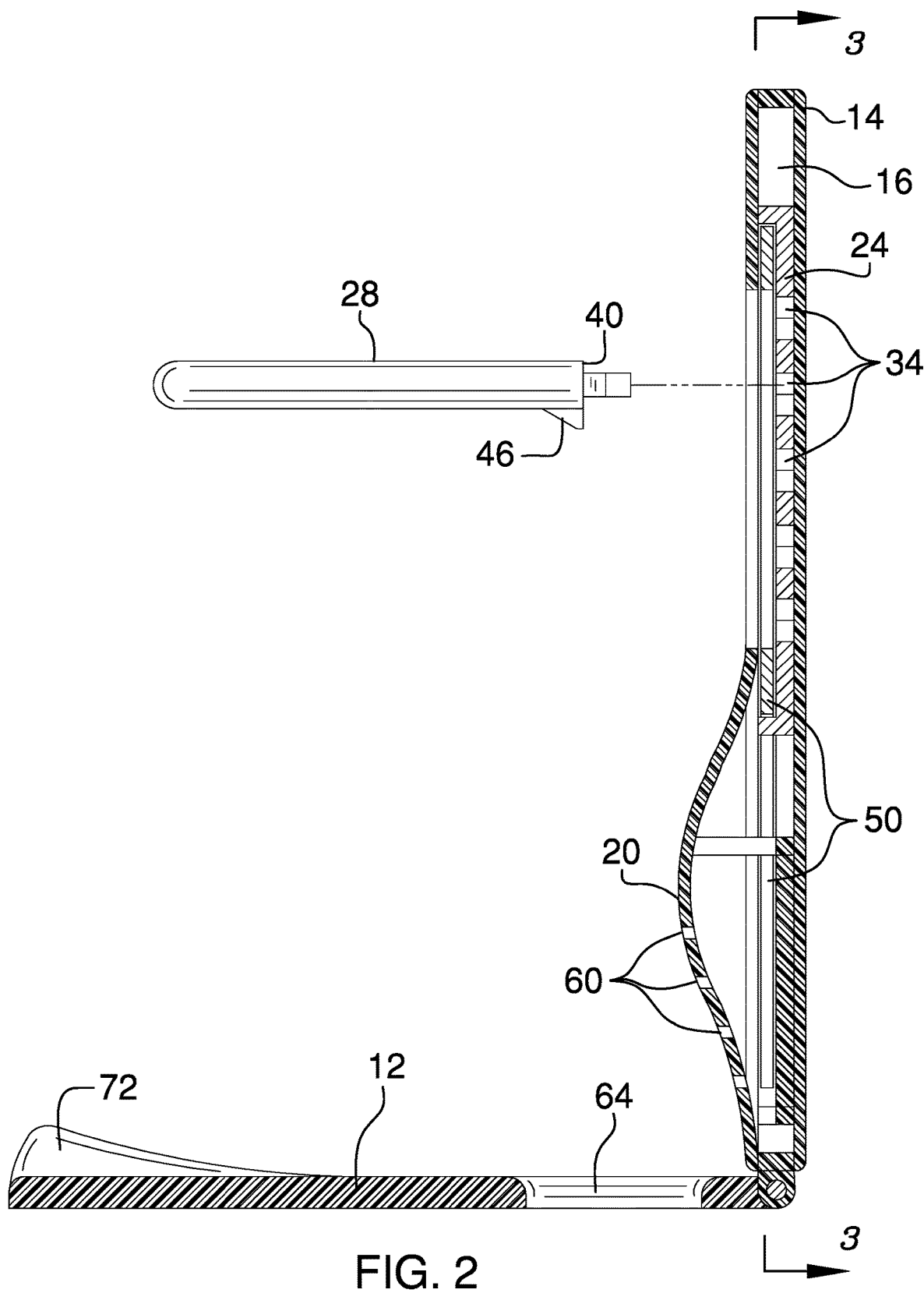
FIG. 2 is a cross-sectional view of an embodiment of the disclosure.

Each of a pair of gussets 46 is coupled to a respective arm 28 proximate to the terminus 40, as shown in FIG. 2, so that the gusset 46 is positioned to brace the arm 28 relative to the plate 24.

An actuator 48 is positioned in the interior space 16. The actuator 48 is operationally coupled to the plate 24 so that the actuator 48 is positioned to selectively raise the plate 24 relative to the seat of the chair. The coupling means 26 is configured to transmit an upward force from the actuator 48 to the torso of the user to place a lumbar region of a spine of the user in traction.

Figure 3:
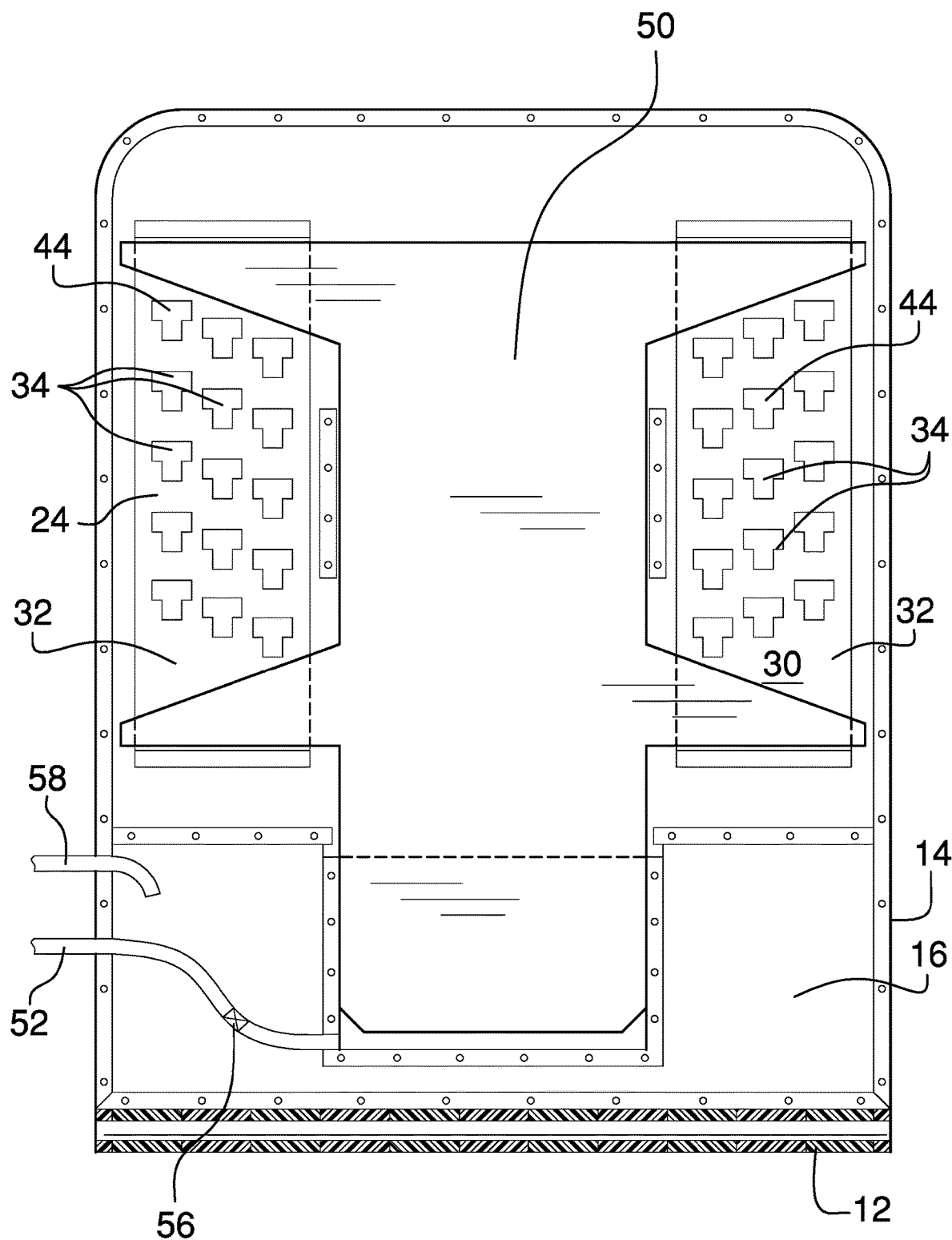
FIG. 3 is a cross-sectional view of an embodiment of the disclosure.
Figure 4:
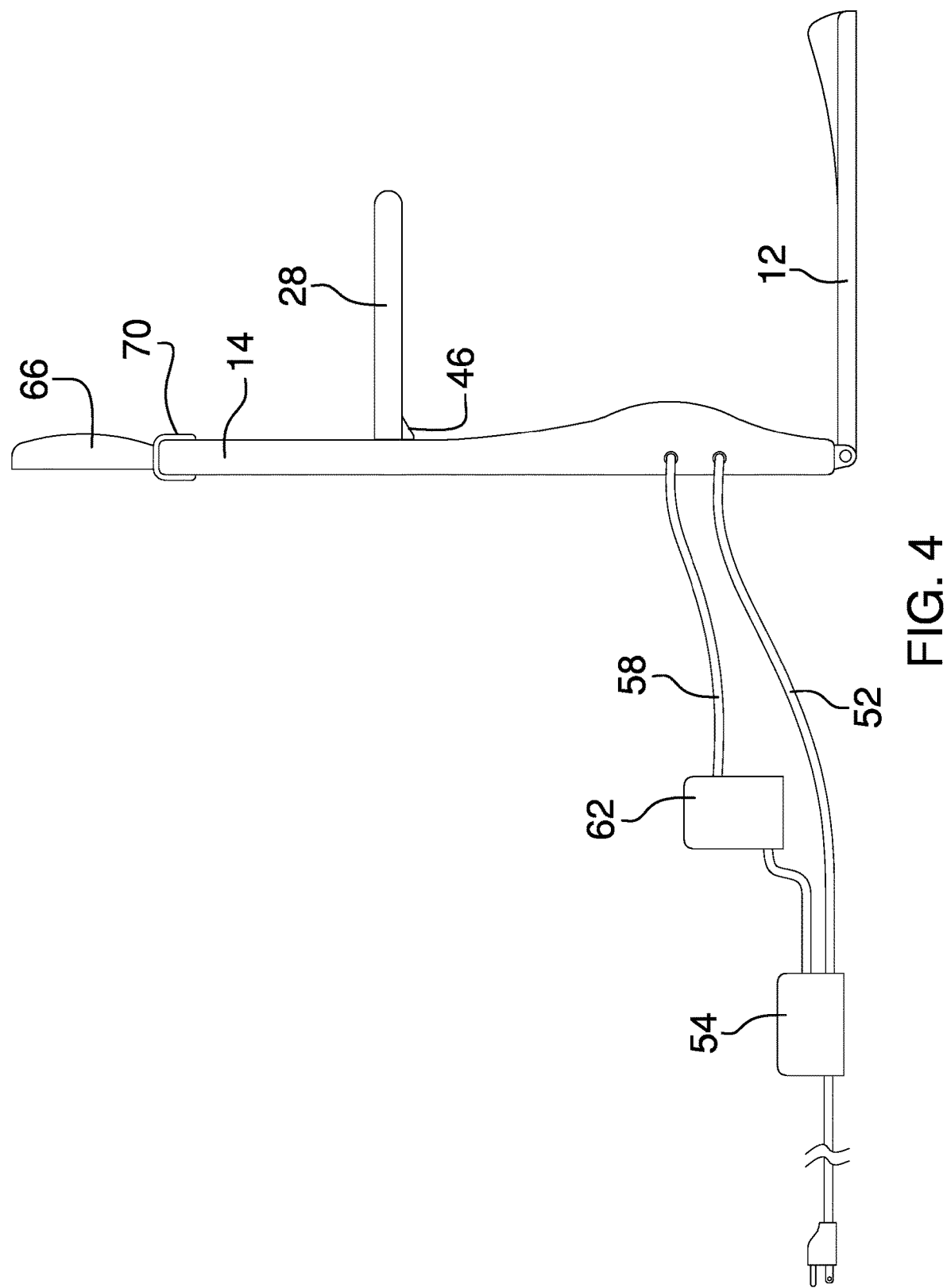
FIG. 4 is a side view of an embodiment of the disclosure.

The actuator 48 may comprise a piston 50 that is air actuated type, or other actuating means, such as, but not limited to, hydraulic cylinders, motorized rack gear assemblies, and the like. A hose 52 is operationally coupled to and extends from the piston 50, as shown in FIG. 4. A pump 54 is operationally coupled to the hose 52 distal from the piston 50 so that the pump 54 is positioned to selectively force air through the hose 52 to actuate the piston 50. A valve 56 that is positioned inline with the hose 52, as shown in FIG. 3, is configured to prevent over pressurization of the piston 50.

A tube 58 is coupled to and extends between the pump 54 and the shell 14 so that the tube 58 is in fluidic communication with the interior space 16. A plurality of holes 60 is positioned in the lower section 20 of the front 22 face of the shell 14. The plurality of holes 60 is configured to allow air to escape from the interior space 16 onto the lower back of the user.

A heating and cooling module 62 may be positioned inline with the tube 58, as shown in FIG. 4. The heating and cooling module 62 is configured to selectively heat and cool the air that passes through the tube 58 so that the air selectively heats and cools the lower back of the user.

A cutout 64 is positioned in the panel 12 proximate to the shell 14. The cutout 64 is configured to insert a tailbone of the user who is seated upon the chair to minimize pressure on the tailbone.

A headrest 66 that is selectively couplable to an upper end 68 of the shell 14 is configured to support a head of the user who is seated upon the chair. A pair of clips 70 that is coupled to the headrest 66 is positioned to selectively couple to the shell 14 to removably couple the headrest 66 to the shell 14. The present invention anticipates other fastening means for coupling the headrest 66 to the shell 14, such as, but not limited to, hook and loop fasteners, snap closures, and the like.

A protrusion 72 is coupled to and extends from an upper face 74 of the panel 12 distal from the shell 14. The protrusion 72 is positioned equally distant from opposing edges 76 of the panel 12 and is configured to contour the panel 12 to enhance comfort of the user.

Figure 5:
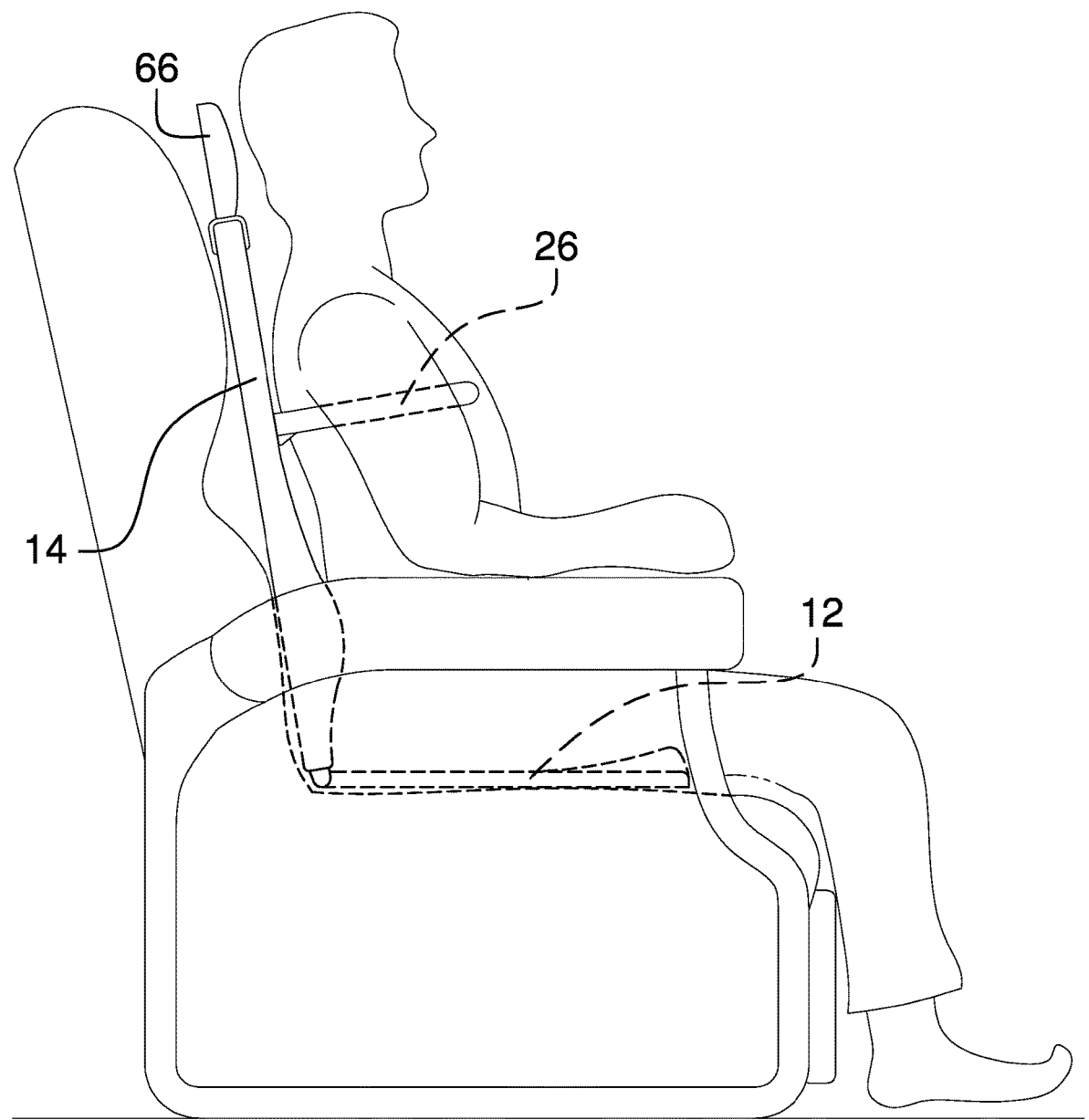
FIG. 5 is an in-use view of an embodiment of the disclosure.
Figure 6:
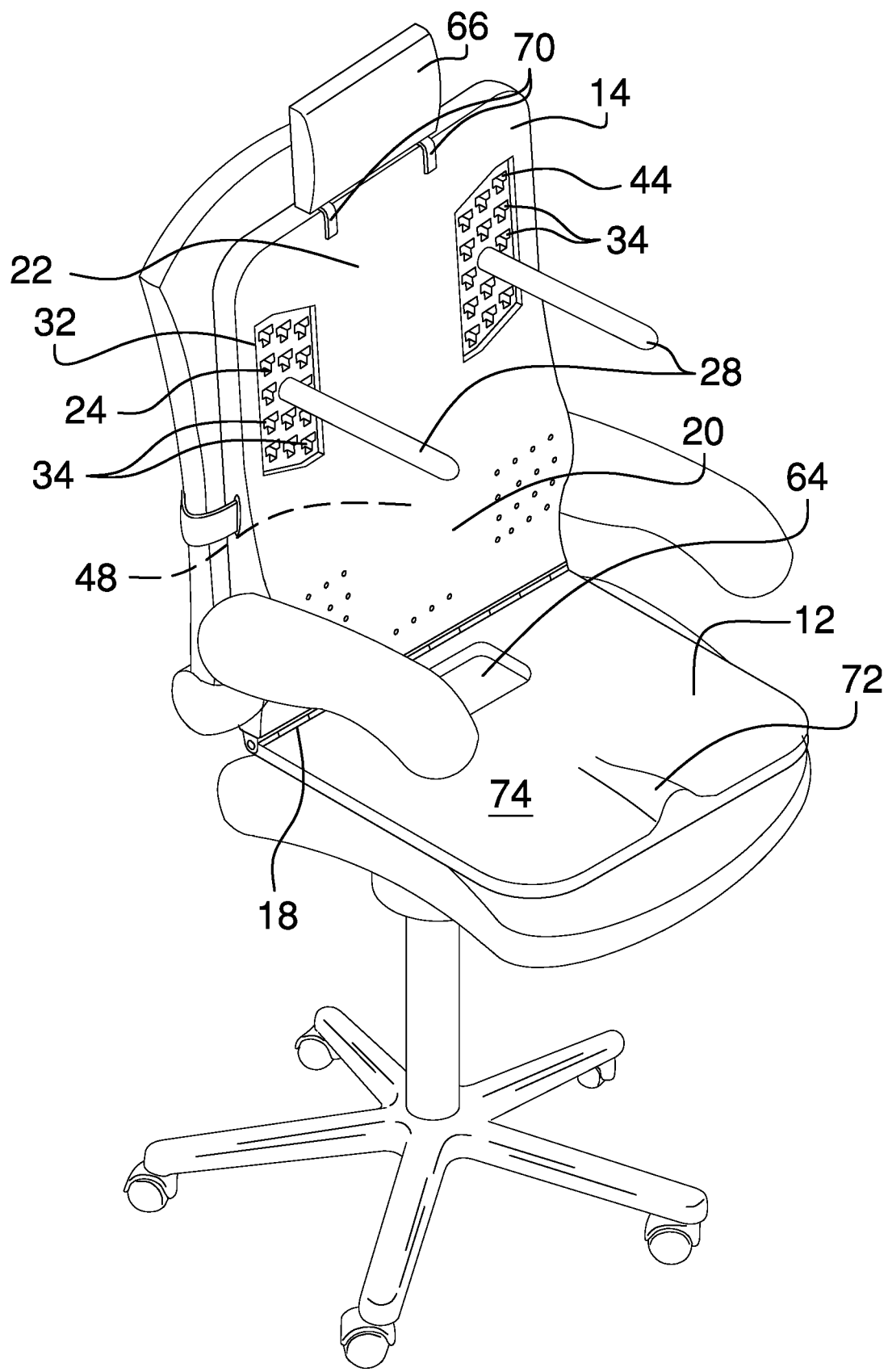
FIG. 6 is an isometric perspective view of an embodiment of the disclosure.

In use, the panel 12 is positioned on the seat of the chair with the shell 14 in abutment to the backrest of the chair. Each arm 28 is coupled to the plate 24 by inserting the bar 42 into a respective slot 44 so that the arm 28 is configured to be inserted into an associated armpit of the user, as shown in FIG. 5. The pump 54 then is engaged to force the air through the hose 52 to actuate the piston 50 to raise the plate 24 relative to the seat. The arms 28 transmit the upward force from the piston 50 to the torso of the user, causing the lumbar region of the spine to be placed in traction.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A lumbar traction device comprising:
    a panel configured for positioning on a seat of a chair;
    a shell defining an interior space, the shell being coupled to and extending from a rear edge of the panel wherein the shell is configured for positioning in abutment to a backrest of the chair;
    a plate positioned in the interior space;
    a coupling means coupled to the plate and extending through a front of the shell wherein the coupling means is configured for coupling to a torso of a user seated upon the chair for coupling the user to the plate; and
    an actuator positioned in the interior space, the actuator being operationally coupled to the plate such that the actuator is positioned for selectively raising the plate relative to the seat of the chair wherein the coupling means is configured for transmitting an upward force from the actuator to the torso of the user for placing a lumbar region of a spine of the user in traction.

2. The device of claim 1, further including the shell being hingedly coupled to the panel wherein the shell is configured for hinging relative to the panel as the backrest is hinged relative to the seat.

3. The device of claim 1, further including a lower section of the front of the shell being convexly arcuate wherein the lower section is configured for supporting a lower back of the user.

4. The device of claim 1, further including the coupling means comprising a pair of arms, each arm being coupled to and extending from a forward face of the plate through an associated orifice positioned in the shell wherein the arm is configured for positioning in an associated armpit of the user seated upon the chair.

5. The device of claim 4, further comprising:
a set of first fasteners, each first fastener being coupled to the plate such that the first fastener is accessible through an associated orifice positioned proximate to an associated opposing side of the shell; and
a pair of second fasteners, each second fastener being coupled to a terminus of a respective arm, the second fastener being complementary to the first fasteners such that the second fastener is positioned for selectively coupling to a respective first fastener for removably coupling the respective arm to the plate such that the respective arm is positioned for inserting into the associated armpit of the user.

6. The device of claim 5, further comprising:
the second fastener comprising a bar coupled to and extending from the terminus of the respective arm, the bar being T-shaped; and
the respective first fastener comprising a slot positioned in the plate, the slot being T-shaped such that the slot is positioned for selectively inserting the bar for removably coupling the respective arm to the plate.

7. The device of claim 5, further including a pair of gussets, each gusset being coupled to a respective arm proximate to the terminus such that the gusset is positioned for bracing the arm relative to the plate.

8. The device of claim 1, further comprising:
the actuator comprising a piston, the piston being air actuated type;
a hose operationally coupled to and extending from the piston; and
a pump operationally coupled to the hose distal from the piston such that the pump is positioned for selectively forcing air through the hose for actuating the piston.

9. The device of claim 8, further including a valve positioned inline with the hose wherein the valve is configured for preventing over pressurizing of the piston.

10. The device of claim 8, further comprising:
a tube coupled to and extending between the pump and the shell such that the tube is in fluidic communication with the interior space; and
a plurality of holes positioned in the lower section of the front of the shell wherein the plurality of holes is configured for exiting of air from the interior space onto the lower back of the user.

11. The device of claim 10, further including a heating and cooling module positioned inline with the tube wherein the heating and cooling module is configured for selectively heating and cooling the air passing through the tube such that the air selectively heats and cools the lower back of the user.

12. The device of claim 1, further including a cutout positioned in the panel proximate to the shell wherein the cutout is configured for inserting a tailbone of the user seated upon the chair for minimizing pressure on the tailbone.

13. The device of claim 1, further including a headrest selectively couplable to an upper end of the shell wherein the headrest is configured for supporting a head of the user seated upon the chair.

14. The device of claim 13, further including a pair of clips coupled to the headrest such that each clip is positioned for selectively coupling to the shell for removably coupling the headrest to the shell.

15. The device of claim 1, further including a protrusion coupled to and extending from an upper face of the panel distal from the shell, the protrusion being positioned equally distant from opposing edges of the panel wherein the protrusion is configured for contouring the panel for enhancing comfort of the user.

16. A lumbar traction device comprising:
a panel configured for positioning on a seat of a chair;
a shell defining an interior space, the shell being coupled to and extending from a rear edge of the panel wherein the shell is configured for positioning in abutment to a backrest of the chair, the shell being hingedly coupled to the panel wherein the shell is configured for hinging relative to the panel as the backrest is hinged relative to the seat, a lower section of a front of the shell being convexly arcuate wherein the lower section is configured for supporting a lower back of the user;
a plate positioned in the interior space;
a coupling means coupled to the plate and extending through the front of the shell wherein the coupling means is configured for coupling to a torso of a user seated upon the chair for coupling the user to the plate, the coupling means comprising a pair of arms, each arm being coupled to and extending from a forward face of the plate through an associated orifice positioned in the shell wherein the arm is configured for positioning in an associated armpit of the user seated upon the chair;
a set of first fasteners, each first fastener being coupled to the plate such that the first fastener is accessible through an associated orifice positioned proximate to an associated opposing side of the shell;
a pair of second fasteners, each second fastener being coupled to a terminus of a respective arm, the second fastener being complementary to the first fasteners such that the second fastener is positioned for selectively coupling to a respective first fastener for removably coupling the respective arm to the plate such that the respective arm is positioned for inserting into the associated armpit of the user, the second fastener comprising a bar coupled to and extending from the terminus of the respective arm, the bar being T-shaped, the respective first fastener comprising a slot positioned in the plate, the slot being T-shaped such that the slot is positioned for selectively inserting the bar for removably coupling the respective arm to the plate;
a pair of gussets, each gusset being coupled to a respective arm proximate to the terminus such that the gusset is positioned for bracing the arm relative to the plate;
an actuator positioned in the interior space, the actuator being operationally coupled to the plate such that the actuator is positioned for selectively raising the plate relative to the seat of the chair wherein the coupling means is configured for transmitting an upward force from the actuator to the torso of the user for placing a lumbar region of a spine of the user in traction, the actuator comprising a piston, the piston being air actuated type;
a hose operationally coupled to and extending from the piston;
a pump operationally coupled to the hose distal from the piston such that the pump is positioned for selectively forcing air through the hose for actuating the piston;
a valve positioned inline with the hose wherein the valve is configured for preventing over pressurizing of the piston;
a tube coupled to and extending between the pump and the shell such that the tube is in fluidic communication with the interior space;

a plurality of holes positioned in the lower section of the front of the shell wherein the plurality of holes is configured for exiting of air from the interior space onto the lower back of the user;

a heating and cooling module positioned inline with the tube wherein the heating and cooling module is configured for selectively heating and cooling the air passing through the tube such that the air selectively heats and cools the lower back of the user;

a cutout positioned in the panel proximate to the shell wherein the cutout is configured for inserting a tailbone of the user seated upon the chair for minimizing pressure on the tailbone;

a headrest selectively couplable to an upper end of the shell wherein the headrest is configured for supporting a head of the user seated upon the chair;

a pair of clips coupled to the headrest such that each clip is positioned for selectively coupling to the shell for removably coupling the headrest to the shell; and a protrusion coupled to and extending from an upper face of the panel distal from the shell, the protrusion being positioned equally distant from opposing edges of the panel wherein the protrusion is configured for contouring the panel for enhancing comfort of the user.

* * * * *